United States Patent
Genkin et al.

(10) Patent No.: US 7,718,589 B2
(45) Date of Patent: May 18, 2010

(54) METHOD FOR WASHING THE FACE SKIN AND A COMPOSITION FOR CARRYING OUT SAID METHOD

(76) Inventors: Dmitry Dmitrievich Genkin, Konstantinovsky pr., d.26, kv. 1, Saint-Petersburg (RU) 197110; Viktor Veniaminovich Tets, ul. Lensoveta, d.27, kv. 95, Saint-Petersburg (RU) 196066; Georgy Viktorovich Tets, ul. Pushkinskaya, d.13, kv. 41, Saint-Petersburg (RU) 191025

( * ) Notice: Subject to any disclaimer, the term of this patent is extended or adjusted under 35 U.S.C. 154(b) by 170 days.

(21) Appl. No.: 11/995,986

(22) PCT Filed: Jul. 18, 2005

(86) PCT No.: PCT/RU2005/000389

§ 371 (c)(1),
(2), (4) Date: Jan. 17, 2008

(87) PCT Pub. No.: WO2007/011253

PCT Pub. Date: Jan. 25, 2007

(65) Prior Publication Data

US 2009/0143268 A1      Jun. 4, 2009

(51) Int. Cl.
*A61Q 8/64* (2006.01)
(52) U.S. Cl. .............. 510/157; 424/70.15; 424/70.17; 8/406
(58) Field of Classification Search ........... 510/157; 424/70.15, 70.17; 8/406
See application file for complete search history.

(56) References Cited

U.S. PATENT DOCUMENTS

| | | | | |
|---|---|---|---|---|
| 6,337,066 | B1 * | 1/2002 | Jacquier | 424/69 |
| 6,649,176 | B1 * | 11/2003 | Shapiro et al. | 424/401 |
| 2005/0025736 | A1 * | 2/2005 | Jachowicz et al. | 424/70.15 |
| 2009/0143268 | A1 * | 6/2009 | Genkin et al. | 510/137 |

FOREIGN PATENT DOCUMENTS

| CN | 1323577 | * | 11/2001 |
|---|---|---|---|
| JP | 2004115405 A | * | 4/2004 |

* cited by examiner

*Primary Examiner*—Milton I Cano
*Assistant Examiner*—M. Reza Asdjodi
(74) *Attorney, Agent, or Firm*—John D. Cucliotta, PE, ESQ

(57) ABSTRACT

The inventions relate to hygiene and cosmetology, in particular to skin care. The inventive method for washing the skin by applying washing or cleaning agents and water is characterized in that it uses water with pH level ranging from 3.0 to 6.0, wherein the water flow rate ranges from 0.1 to 5 ml per 1 $cm^3$ of the skin surface. The inventive composition comprises water, mineral salts and oxygen dissolved in said water, and also one or several types of essential proteinogenic amino acids with isoelectric point ranging from 3.0 to 6.0 pH, and its hardness is equal to or less than 0.5 mg-equivalent unit/$dm^3$. The inventive method and composition make it possible to correct complex unfavourable changes of the skin surface layers by providing it with the required pH values during and after the washing and also by maintaining the normal chemical and bacteriological condition of the face skin.

3 Claims, No Drawings

METHOD FOR WASHING THE FACE SKIN AND A COMPOSITION FOR CARRYING OUT SAID METHOD

TECHNICAL FIELD

The inventions relate to hygiene and cosmetology and can be used for daily washing, mainly of the face skin, and of other skin areas as well.

BACKGROUND ART

Daily washing of the face skin is one of the primary hygienic procedures of a present-day human. Water is one of the main components of the face skin washing procedure. In developed countries people use water from centralized water supply sources for the washing procedure. Due to the important hygienic role of water its quality is rigorously standardized and controlled. Table 1 lists the main hygienic parameters of water established by Russian Federation. European Union. the USA and the World Health Organization (WHO) for centralized water supply sources.

The standards listed below are justified when applied to potable water; however, they are not suitable if the water in question is used for washing of skin.

The surface skin level is known to have a weak-acid pH reaction within the range of 4.0-6.0 (Analysis of circadianand ultradian rhythms of skin surface properties of face and forearm of healthy women. Le Fur l. Reinberg A., Lorez S., Morizot F., Mechkouri M.. Tschachler E., J. Invest Dermatol, 2001, September, 117:3, pp. 718-724). Problem skin can have the pH parameter shifted in the alkaline direction. This is caused by perspiration disorders in the skin folding regions, activity of certain bacteria and several other factors (Baseline biophysical parameters in subjects with sensitive skin, Seidenari S., Francomano M., Mantovani L., Contact Dermatits, 1998, June, Vol. 38, pp. 311-315). Common hygienic procedures can alter the pH level of skin, too. For example, after three minutes of washing the skin with soap its pH level is shifted in the direction of weak-alkaline values, whereupon at least three or four hours are required for the skin to restore its normal acidity. Even simple washing of the face skin bat means of water with almost neutral acidity parameter (thermal water common tap water, water purified by means of ion-exchange resin or reverse osmosis system) results in prolonged increase of skin acidity level above pH 6.0. This weakens the antimicrobial parameters of skin, which, in particular, is a consequence of inhibition of the normal microflora of skin that happens when the pH parameter is shifted to the direction of neutral and alkaline values; other consequences are the swelling of the skin, accelerated formation of microcrystals of salts that damage the skin, disorders of the epidermis cells functioning (Effects of soap and detergents on skin surface pH, stratum corneum hydration and fat content in infants, Gfatter R., Hackl R., Braun F., Dermatology, 1997, Vol. 195, pp. 258-262).

After washing the skin with hard water its surface accumulates salts of calcium, magnesium and ferrum that are formed in hard water when the ions of calcium, magnesium and ferrum interact with soap. Such salts are not soluble in water, and their crystals seriously damage the skin. The hardness of water can be reduced by boiling, freezing-out, purification by means of ion-exchange filters or reverse osmosis, but the resulting water has reduced osmotic pressure (hyposmolarity).

Table 2 gives the indices of water purification provided by the RO-(reverse-osmosis) membrane.

The use of hyposmolar deionized water during hygienic procedures results in violation of the colloid structure of the epidermis and the protective water-lipidic mantle.

Another important consequence of violation of physiological level of the skin pH is the chemical blockade of amino acids that takes place upon increase of the pH level of skin and disrupts its hydration (Damage to the skin by repetitive washing, Grunewald A. M., Gloor M., Gehring W., Kleesz P., Contact Dermatitis, 1995. Vol. 32, pp. 225-232).

Some known methods of washing the face skin consist in applying shampoo and water (see GB, A1, 908888) or soap and water (see CN, C, 1425749).

Another known method of washing the skin of the face and other areas consists in using soap and common water with pH level that is close to the neutral value (see U.S. Pat. No. 6,559,110).

This engineering solution is taken as a prototype of the current invention—method.

Soap contains substances intended for adjusting the pH level of the skin. The disadvantage of the prototype and other analogous inventions mentioned above consists in that the washing or cleaning agent quickly becomes diluted with water, whereupon its pH level changes from the range of acid values 2.0-6.0 to the neutral direction. The pH of the surface layer of skin also becomes close to neutral value, within the range of 6.0-7.0 pH.

Mineral thermal waters are generally known, such as for example the Vichy thermal water, which has the following properties: calming effect on sensitive skin, anti-edematous and anti-hyperemic effects. Such water reinforces the protective functions of skin and is used in the morning and evening for finishing the hygiene of sensitive face skin, and also during the day as a refreshing agent; the water is sprayed upon the face and then dried with a tissue.

The disadvantage of this water consists in its high mineralization (over 5 g per 1 litre of water). The main components of the mineralization are magnesium, potassium, sodium, manganese and ferrum.

Another widely known thermal water is the thermal water "Laboratoires Biorga" (France). Such water is recommended for daily use for sensitive and hypersensitive skin of newborns, children and adults. The Uriage thermal water, natural isotonic water, is also widely known. It is in perfect osmotic balance with the epidermis cells and their natural medium. Unique concentration of mineral elements makes the Uriage water an excellent agent for treating the face skin: it calms the skin, reduces redness, moisturizes upper layers of epidermis and reinforces natural protective mechanisms of skin. The water is sprayed upon the face skin.

The disadvantage of this water consists in high percentage of calcium and magnesium ions, and in its near neutral pH level.

Thus, the provided data show that the general disadvantage of thermal waters consists in high mineralization and non-physiological pH, which doesn't allow using them as agents for washing the face skin. As a result, thermal waters are used mostly for hydration of the face skin.

Another known application of thermal water consists in using it for reducing the side effects of keratolytic agents incorporated therein (see RU, C. 2131254).

During washing of the skin the oxygen contained in the skin is depleted, the amino acid and microbiological balance of skin is broken. The amount of oxygen dissolved in the water plays an important part in maintaining normal metabolic processes in upper layers of epidermis. The water used in central water supply has low content of dissolved oxygen. This is caused by various reasons: the water is taken either from underground (artesian) layers where the water has low oxygen content from the beginning, or from surface reservoirs with low purity level. Further loss of oxygen takes place during transportation of water through the piping and is caused by oxidation of ferrum and other chemical components of water and the piping system. The use of water with low content of oxygen for daily hygienic procedures may result in intensification of anaerobic processes in the epidermis cells and the microbial colonies of the skin, which is not natural for normal skin.

Amino acids are formed from the keratin of the corneal layer dissolved in water. Amino acids represent one of the main components of the so called Natural Moisturizing Factor. Ionization of the majority of essential amino acids at pH>6.0 results in disorder of their circulation in the surface layers of skin; the washing-off of the amino acids disrupts the hydration and the buffering properties of the skin.

Thus, the process of washing the face skin comprises serious and versatile chemical, biochemical and biological alterations in surface layers of the face skin. Constant influence of this factor can deplete adaptation capabilities of surface layers of skin, resulting in cosmetic defects, diseases of skin and accelerated skin ageing.

A known composition for washing the face skin comprises sodium laureth sulphate, cocamidopropylbetaine, laurylglucoside, PEG-7, glyceryl cocoate, moisturizing admixtures, 40% solution of NTO-55 propyleneglycololeate in propyleneglycol, PEG-40, hydrogenated castor oil, disodium salt ethylenediamine —N,N,N,N,— of 2-water tetraacetic acid, extra or first-class edible citric acid, germabene II. perfume composition, colorants and potable water, bioactive supplements and triclosan, distilled glycerin or propyleneglycol (see RU, C, 2179844).

This composition has an irritating and allergenic influence upon the skin; the detergents adsorbed on the skin surface during the washing prevent normal regeneration of integrity of the protective water-lipidic mantle. This results in increased sensitivity of skin towards negative effects of ultraviolet radiation. The antiseptics contained in the composition strike not only pathogenic and opportunistic pathogenic microorganisms, but also microorganisms that form part of the normal microflora of skin. In natural conditions the normal microflora of skin has an inhibitory effect on the development of microorganisms that are alien for it. Skin that is damaged during the washing and has disturbed microbial balance becomes especially sensitive towards infection with alien microorganisms, including microorganisms contained in the water that is used for washing the face skin.

Another known composition for washing the face skin is produced by dissolving a suspension of deer's placenta in boiled water with subsequent quick freezing and thawing (see CN, 1221606).

The disadvantage of this water consists in its non-physiological pH, which is near the neutral level. Regular use of this water leads to alkalization of the face skin surface.

Yet another known composition for washing the face skin comprises water, mineral salts and dissolved oxygen, and has the capacity of increasing the content of oxygen in the face skin (see DE, A1, 4236607). The composition constitutes a water emulsion that contains from 1 to 8% of weight of nonionic surfactant as an emulsifier and from 0.05 to 100% of weight of oxygen-binding fluorocarbon compounds.

This engineering solution is taken as a prototype of the current invention—composition.

The disadvantage of said composition consists in toxicity and low stability of fluorocarbon compounds, inhibition of energy metabolism of the skin cells, which is caused by the presence of fluorocarbon compounds (Riess J. G., Rev. Fr. Transfus Hemobiol. 1992, Vol. 35, p.p. 391-406; Faradji., et. al., Rev. Fr. Transfus Immunohematol, 1979, Vol. 22, p.p. 119-133: Reichlet H., et. al., Biomater Artif Cells Immobilization biotechnol, 1992, Vol. 20, p.p. 1021-1023). Furthermore, said composition neither provides the required pH values for the face skin nor supports the amino acid and microbiological balance of the face skin.

SUMMARY OF THE INVENTION

In is an object of the present inventions to provide a solution for creating a method and a composition for washing the face skin that make it possible to prevent and/or correct complex unfavourable changes of the face skin surface layers by providing it with the required pH values during and after the washing and also by maintaining the normal chemical and bacteriological condition of the face skin. The solution also reduces the toxicity and increases the stability of the composition, and prevents the inhibition of energy metabolism of the skin cells.

According to the first invention the method for washing the face skin, as well as other skin areas, by applying washing or cleaning agents and water, uses water with pH level ranging from 3.0 to 6.0, wherein the water flow rate ranges from 0.1 to 5 ml per 1 $cm^2$ of the skin surface.

According to the second invention the composition for washing the face skin, which comprises water, mineral salts and oxygen dissolved in said water, additionally comprises one or several types of essential proteinogenic amino acids with isoelectric point ranging from 3.0 to 6.0 pH, with the following ratio of the ingredients (% of weight):

mineral salts—from 0.01 to 0.1;
essential proteinogenic amino acids—from 0.01 to 1;
oxygen dissolved in the water—more than 0.001 at a temperature of 22° C.;
water—the remainder,
wherein the composition has the pH level ranging from 3.0 to 6.0 and its hardness is equal to or less than 0.5 mg-equivalent unit/$dm^3$.

The composition can additionally comprise ascorbic acid in the amount of between 0.0001 and 10 (% of weight), and also provitamin B5 in the amount of between 0.0001 and 10; furthermore, the composition can additionally comprise a mixture of bacteria representing the normal microflora of human skin, including *S. coagulase* (−), *Aerococcus viridans, Bacillus* spp, *Burkholderia cepacia, Corynebacterium* spp, *Acinrtobacter* spp, *Peptostreptococcus* spp: *Propionbacterium* spp, *Veillonella* spp in various combinations thereof and in the amounts ranging from $5-10^{-1}$ to $10 \times 10^{10}$ CFU (colony-forming units) in 1 ml.

The applicant has no information on any methods for washing the skin of the face and other areas of the skin coverlet that uses water with pH level ranging from 3.0 to 6.0, wherein the water flow rate ranges from 0.1 to 5 ml per 1 $cm^2$ of the skin surface. This enables to conclude that the inventive method conforms to the criterion "Novelty" (N).

Realization of the novel features of the inventive method provides the object with important new properties which consist in that the shift of the pH of both the washing or cleaning agent and the face skin to the direction of neutral or weak-alkaline values is prevented, which preserves the pH level of the skin within the physiological norm range 3.0-6.0 during and after the washing, also the impurities are efficiently removed from the skin surface without any irritating or allergenic influence upon the skin. The abovementioned novel features of the invention enable to conclude that the inventive method conforms to the criterion "Inventive Step" (IS).

The applicant hasn't found any sources of information containing data on compositions identical to the present invention. In applicant's opinion, this enables to conclude that the invention conforms to the criterion "Novelty" (N).

Realization of the novel features of the invention provides an efficient solution for creating a composition for washing the face skin that can prevent and/or correct in a complex manner the main negative consequences of washing the face skin; the created composition does not contain tensides or other synthetic agents, which makes it low-irritative and hypoallergic.

In order to prevent the increase of the face skin acidity out of the physiological norm range pH>6.0 during and after the washing, the composition is based on water with acidity level pH within the range of 3.0-6.0. A composition with pH>6.0 cannot prevent the increase of the face skin pH out of the physiological norm range pH6.0 during and after the washing; the use of water with pH<3.0 as a basis for the composition has an irritative influence on the face skin.

In order to prevent hypo-oxygenation of the skin surface layers, the invention uses oxygen-enriched water. Oxygen-enriched water that contains more than 90% of dissolved oxygen satisfies physiological need for oxygen, which amounts to about 100 µg of oxygen per 1 $cm^2$ of the face skin surface.

In order to prevent the formation of insoluble salts, the composition is based on water with low contents of ions of calcium, magnesium and ferrum. The content of the above-mentioned ions, which forms the overall hardness of the water, is equal to or less than 0.5 mg-equivalent unit/$dm^3$.

In order to prevent undesirable osmotic effects, the overall mineralization of the composition lies within the physiological limits—100-1000 mg/litre.

In order to correct the imbalance of the amino acids content, the composition comprises one or more essential proteinogenic amino acids with isoelectric point ranging from 3.0 to 6.0 pH, in particular: valine, leucine, methionine, phenylalanine, tryptophan.

The fact that the pH of the face skin remains within the physiological norm range pH3.0-6.0 during and after the washing ensures efficient penetration of essential proteinogenic amino acids, which have isoelectric point within this range, into the surface layers of skin. Amino acids are included into the composition in the amount of 0.01 to 1% of weight, which helps maintain the physiological level of their concentration in the skin surface layers.

Additionally, in order to correct the photosensibilizing action of exogenous tensides, in particular detergents, the composition can also comprise ascorbic acid in the amount from 0.0001 to 10% of weight. Such concentrations of ascorbic acid have pronounced photoprotective effect.

Additionally, in order to prevent the development of skin dysbacteriosis, the composition can also comprise bacteria representing the components of the normal microflora of human skin: *S. coagulase* (−), *Aerococcus viridans*, *Bacillus* spp, *Burkholderia cepacia*, *Corynebacterium* spp, *Acinrtobacter* spp, *Peptostreptococcus* spp, *Propionbacterium* spp, *Veillonella* spp in various combinations thereof and in the amounts ranging from $5 \cdot 10^{-1}$ to $10 \times 10^{10}$ CFU in 1 ml.

The applicant hasn't found any sources of information containing data on the influence of the inventive features on the technical result produced through the realization of said features. In applicant's opinion, this enables to conclude that the present engineering solution conforms to the criterion "Inventive Step" (IS).

BRIEF DESCRIPTION OF THE DRAWINGS

The inventions are further explained, by way of example, without reference to any drawings.

PREFERRED EMBODIMENT

The inventive method is explained by means of the following examples.

EXAMPLE 1

A comparative investigation of ability of the prototype and the method of the present invention to maintain the acidity parameters of the face skin within the physiological limits after the washing was conducted.

Five women from the Group 1 used tap water for the prototype method. Five women from the Group 2 used a common cleansing lotion, tap water and finished the procedure with application of a tonic. Women from the Groups 3, 4 and 5 (each group contained 5 women) used the method according to the present invention, i.e. applied washing or cleaning agents together with water having pH level from 3.0 to 6.0, and the water flow rate ranging from 0.1 to 5 ml per 1 $cm^2$ of the skin surface. The required pH level was ensured by passing carbon dioxide through the tap water.

The initial pH parameter of the face skin was measured during the washing and right after the completion of the hygienic procedure. Women from the Group 3 used water with pH 3.0 and water flow rate 0.1 $mm/cm^2$, women from the Group 4—pH 4.5 and water flow rate 2.5 $mm/cm^2$, women from the Group 5—pH 6.0 and water flow rate 5 $mm/cm^2$.

The results of the experiment are shown in Table 3.

The data of Table 3 show that the usage of the prototype method does not prevent the increase of the pH parameter outside the physiological limits of pH. Application of an acidulous tonic after using the water is incapable of reducing the pH parameter to the limit value of the physiological norm. The usage of the method according to the present invention maintains the pH parameter of the face skin within the physiological limits both during the washing and after its completion.

EXAMPLE 2

The realization of the method used tap water that was acidulated by means of hydrochloric acid and had pH of 4.5

10 litres of tap water taken from the river Neva basin were subjected to deionization by means of the Millipore 2000 plant with subsequent filtration through a filter with pore diameter of 0.22 µm.

A comparative investigation was conducted in two groups of women aged from 16 to 45 (each group consisted of 10 women), which compared the inventive method and the prototype method during four-week daily washing of the face skin performed twice a day. Tap water (10 women from the Group 1) and the water used in the method according to the present invention in the amount of 3 $ml/cm^2$ of skin (10 women from the Group 2) were bottled into 1-litre plastic bottles without any labels.

At the beginning and after the completion of the four-week course an instrumental examination was conducted, with comprised the following procedures: evapometry of the skin, measurement of pH of the face skin, elastometry of the face skin. The results are shown in Table 4.

Thus, the method for washing the skin according to the present invention efficiently restores physiological level of the skin pH, makes the skin more hydrated and elastic.

EXAMPLE 3

In order to determine the range of values of the water flow rate per 1 cm² of the skin surface, the water that was used was acidulated by means of nitric acid until having the pH of 4.5. It should be noted that water with pH<3.0 causes an irritation of skin, while water with pH≧6.0 does not prevent shift of the pH to the direction of alkaline values.

10 litres of water were filtered through a filter with pore diameter of 0.22 μm.

A comparative investigation was conducted in two groups of women aged from 20 to 36. 10 women from the Group 1 used for their daily washing the water with pH of 4.5 bottled into 1-litre plastic bottles without any labels. 10 women from the Group 2 used tap water for their daily washing. Water flow rate in both cases equaled 0.1 ml/cm² of the skin surface. The investigation was conducted during 2 weeks. Before the beginning of the investigation and right after its completion the women were subjected to a testing procedure by means of the DermaView Model-200 device, which allowed detecting any cosmetic defects of the face skin and define the skin fragments that required cosmetic correction. The results are shown in Table 5.

The reference wash-out water samples that were used during the reference test 2 were obtained after washing the face skin by means of a washing lotion with subsequent application of 1 litre of tap water. The reference wash-out water samples that were used during the reference test 3 were obtained after superficial cleaning of the skin by means of a cleaning cream and an alcohol-free tonic. During the determination of the water flow rate in the method according to the present invention (test 1) that must be applied to the skin in order to efficiently remove all impurities from the skin surface, after applying the washing or cleaning agent the skin was washed by various amounts of water, whereupon a reference wash-out was obtained by applying 5 ml of distilled water upon 10 cm² of the face skin surface. The wash-out water samples were plated on solid nutrient mediums in order to determine the rate of microbial contamination, also the influence of said water samples on liberation of carboxifluorescein fluorescent dye from the liposomes (test for the presence of detergents) was studied and the organic sediment of the wash-out water samples was determined. All three tests took into account 3 following parameters: presence of detergents, microbial contamination and organic sediment. The results are shown in Table 6.

Thus, it is obvious that impurities cannot be efficiently removed if the amount of water used during the cleaning of the face skin is less than 0.1 ml of water per 1 cm² of the skin surface. Application of water in the amounts more than 5.0 ml per 1 cm² of the skin surface can lead to undesirable consequences related to removal of components of the normal protective mantle of the skin and of the normal microflora of the skin.

Thus, the method of washing the skin according to the present invention preserves the skin coverlet better than the prototype method.

Preparation and application of the composition for the realization of the method is explained by means of the following examples:

EXAMPLE 4

Composition for washing the skin on the basis of natural artesian water. Artesian water taken from a 400-meter well in the outskirts of the town of Vyborg (Leningradskaya oblast) has overall hardness less than 0.225 mg-equivalent unit/dm³, mineralization of about 400 mg/l and content of ferrum—7.5 μmg per litre. The water has the pH parameter of 6.9. microbial contamination (CFU)—12 per 1 ml, content of oxygen dissolved in the water—less than 80% at a temperature of 22° C. In order to prepare 10 litres of water according to the present invention. 10 litres of artesian water were subjected to filtration through a filter with pore diameter of 0.22 μm and then oxygenized by passing oxygen through the water during 30 minutes under pressure of 1.2 atmosphere inside a glass reactor at a temperature of 25° C. During the final stage the pH of the water was brought to 5.85 inside the same reactor by adding 0.1M solution of ascorbic acid, with constant pH-metry. 1 g/l of methionine amino acid was added. The water was poured into a 10-litre plastic vessel and subjected to analysis 24 hours later.

Water mineralization—400 mg/l
Water hardness—less than 0.225 mg-equivalent unit/dm³
Water acidity—pH 5.85
Oxygen content—more than 0.001
Amino acids—1
Ascorbic acid—0.3
Microbial contamination (CFU)—less than 5 in 1 ml

EXAMPLE 5

Composition for washing the skin on the basis of tap water. 10 litres of tap water with pH of 7.0 were subjected to deionization by means of the Millipore 2000 plant with subsequent filtration through a filter with pore diameter of 0.22 μm. Artificial mineralization was obtained by using a mixture of the Dead Sea salts, which were added at a temperature of 20° C. stirring slowly, until the overall level of mineralization reached 300 mg/l. After that 1 ml of 10% solution of essential amino acids (Aminoplasmal) was added, and the acidity parameter was brought to pH 4.5 by passing carbon dioxide and oxygen through the water under pressure of 1.2 atmosphere and with constant pH-metry. The water was poured into a 10-litre plastic vessel and subjected to analysis 24 hours later.

Water mineralization—300 mg/l
Water hardness—less than 0.150 mg-equivalent unit/dm³
Water acidity—pH 4.5
Oxygen content—more than 0.001
Microbial contamination (CFU)—less than 5 in 1 ml.
Content of amino acids (including valine, leucine, methionine, phenylalanine, tryptophan)—0.01

EXAMPLE 6

Water for washing the skin on the basis of mineral water

Mineral table water "Evian" was used in preparation of water for washing the skin. Water "'Evian", which is bottled from the Source Cachat (France), has mineralization of 309 mg/l, hardness about 0.2 mg-equivalent unit/dm³ and weak-alkaline reaction near pH of 7.2. The analysis showed that the microbial count of the water is more than 5 CFU in 1 ml and the content of dissolved oxygen is less than 90%.

10 litres of water were subjected to filtration through a filter with pore diameter of 0.22 μm and then oxygenized by passing oxygen through the water during 30 minutes under pressure of 1.2 atmosphere inside a glass reactor at a temperature of 25° C. During the final stage the pH of the water was brought to 3.0 inside the same reactor by adding a preliminary prepared 10% solution of ascorbic acid, with constant control by means of pH-metry. Valine, leucine, methionine, phenylalanine, tryptophan were added in the amount of up to 0.1% of weight, dry culture *Propoinbacterium* spp $10 \times 10^3$ CFU in 1 ml. The water was poured into a 10-litre plastic vessel and subjected to analysis 24 hours later.

Water mineralization—310 mg/l
Water hardness—less than 0.2 mg-equivalent unit/dm$^3$
Water acidity—pH 3.0
Oxygen content—more than 0.001
Amino acids—0.1
Microbial contamination (CFU)—30 in 1 ml
Content of ascorbic acid—0.5

Investigation 1

A blind comparative investigation was conducted in two groups of women aged from 20 to 36. 10 women from the Group 1 used composition as described in Example 4 for their daily washing, which was stored in 1-litre plastic bottles without any labels. 10 women from the Group 2 used the prototype composition, moved into 1-litre plastic bottles without any labels. The investigation was conducted during 2 weeks. Before the beginning of the investigation and right after its completion the women were subjected to a testing procedure by means of the DermaView Model-200 device, which allowed detecting any cosmetic defects of the face skin and define the skin fragments that required cosmetic correction. The results are shown in Table 7.

Thus, the composition according to the present invention provides better cosmetic and hygienic effects than the prototype.

Investigation 2

A blind comparative investigation was conducted in three groups of women aged from 16 to 45 (10 women in each group). The investigation studied the influence of tap water, of the prototype composition and the composition as described in Example 5 on the condition of skin after 4 weeks of using them in daily hygienic procedures of washing the face skin. Tap water (10 women from the Group 1), the prototype (10 women from the Group 2) and the composition according to the present invention (10 women from the Group 3) were bottled into 1-litre plastic bottles without any labels.

At the beginning and after the completion of the four-week course an instrumental examination was conducted, with included evapometry of the skin, measurement of pH of the face skin and elastometry of the skin. The results are given in Table 8.

Thus, the composition according to the present invention efficiently restores physiological level of the skin pH, makes the skin more hydrated and elastic as compared to common tap water and the prototype.

Investigation 3

The investigation compared the effect of using the composition as described in Example 6 with the effect of using the prototype composition, tap water, cleansing tonic and cleansing lotion. The investigation was conducted in four groups of women aged from 16 to 35. The constitution of the normal microflora of skin, the acidity parameter of skin, the moisture and elasticity level of the skin coverlet were studied before the beginning of the investigation and 10 days after the application of corresponding washing compositions. The result was expressed in percents of the initial average level, see Table 9.

Thus, it is obvious that among all compositions that were used during the investigations, including the prototype, only the composition according to the present invention can maintain the normal level of acidity of the skin, constitution of its normal microflora and make the skin more hydrated and elastic.

Investigation 4

The investigation was conducted among 15 women aged from 15 to 20 with acne. Women from the Group 1 (5 women) used tap water during the washing procedure. Women from the Group 2 (5 women) used the prototype during the washing procedure. Women from the Group 3 used the composition as described in Example 2 of the present invention during the washing procedure. The investigation was conducted during 3 weeks. The amount of blackheads on the face skin of women from the Groups 1 and 2 remained as before. Women from the Group 3 had the acne amount decreased by 30%.

INDUSTRIAL APPLICABILITY

The realization of the inventive method and the making of the composition are done by means of easy-to-obtain components and known equipment. In applicant's opinion, this enables to conclude that the invention conforms to the criterion "Industrial Applicability" (IA).

Hygienic parameters of water from centralized water supply sources.

TABLE 1

| Parameter | Unit | WHO* | USEPA** | EU*** | SanPiN**** |
|---|---|---|---|---|---|
| pH | pH unit | | 6.5-8.5 | 6.5-8.5 | 6-9 |
| Overall mineralization | mg/liter | <1000 | <500 | <1500 | <1000 |
| Overall hardness | mg-equivalent unit/liter (dm$^3$) | | | <1.2 | <7.0 |

*The World Health Organization (WHO), the Guidelines for Drinking-water Quality (GDWQ), 1984 (review and revised in 1992).
**U.S. Environment Protection Agency, "National Primary Drinking Water Regulations".
***On the 15$^{th}$ of July 1980 the European Community (EC) carried the Drinking Water Directive (80/778/EC), which is responsible for regulating the quality of water in the European Union (EU) intended for human consumption.
****The Russian Federation Sanitary and Epidemiological Regulations and Standards/Sanitary Norms and Rules (SanPiN); the Sanitary Norms and Rules 2.6.1.1281-03 "Drinking Water. Hygienic requirements to the potable water quality in the centralized water supply facilities. Quality control." were approved by the Chief State Health Inspector of the Russian Federation and inured on the 1$^{st}$ of July 1997.

The indices of water purification provided by the RO-(reverse-osmosis) membrane

TABLE 2

| Type of the impurities | Purification extent |
|---|---|
| Mechanical impurities/muddiness | >99% |
| Mineral ones: | |
| Natrium | 90-95% |
| Calcium | 93-98% |
| Magnesium | 93-98% |
| Ferrum | 93-98% |

The results of the comparative investigation conducted to study the ability of the prototype and the method of the present invention to maintain the acidity parameters of the face skin within the physiological limits after the washing.

TABLE 3

| | Before washing | During washing | After washing |
|---|---|---|---|
| Group 1 | 5.6 ± 0.3 | 7.2 ± 0.4* | 6.9 ± 0.25 |
| Group 2 | 5.6 ± 0.3 | 7.1 ± 0.5** | 6.7 ± 0.3*** |
| Group 3 | 5.6 ± 0.3 | 5.7 ± 0.25 | 5.6 ± 0.25 |
| Group 4 | 5.6 ± 0.3 | 5.6 ± 0.25 | 5.6 ± 0.25 |
| Group 5 | 5.6 ± 0.3 | 5.5 ± 0.25 | 5.5 ± 0.25 |

*Measured after the removal of washing or cleaning agents.
**Measured before the application of a tonic.
***Measured after the application of a tonic.

The results of the comparative investigation conducted in two groups of women, which compared the inventive method and the prototype method during four-week daily washing of the face skin performed twice a day

TABLE 4

| | Group 1 | Group 2 |
|---|---|---|
| pH | 6.2 ± 0.3/6.3 ± 0.5 | 6.2 ± 0.3/5.7 ± 0.3 |
| Elastometry, % | 14.3 ± 0.8/13.9 ± 0.6 | 14.3 ± 0.8/16.3 ± 0.9 |
| Moisture content, % | 33.5 ± 2.4/32.5 ± 1.2 | 33.5 ± 2.4/42.5 ± 2.5 |

Each first figure (before slash)—an indice measured at the beginning of the investigation, the second figure (after slash)—an indice measured at the end of the investigation.

The results of the comparative investigation conducted to study the influence of the water with pH 4.5 and the tap water on the face skin.

TABLE 5

The mean percentage of the face skin surface (in the Group), which needs the cosmetic correction

| | Group 1 | Group 2 |
|---|---|---|
| Before said water use | 17.4 | 17.9 |
| In two weeks of said water use | 12.5 | 25.1 |

The results of the investigation of the reference wash-outs

TABLE 6

The organic residues of the wash-out water samples

| | Test 1 | | | | | | Test 2 | Test 3 |
|---|---|---|---|---|---|---|---|---|
| | 0.01 ml/cm² | 0.05 ml/cm² | 0.1 ml/cm² | 1.0 ml/cm² | 5.0 ml/cm² | 10.0 ml/cm² | | |
| Microbial count (CFU) per 1 ml | | 17 | 14 | 16 | 13 | 7 | 15 | 36 |
| Detergents | ++ | + | − | − | − | − | − | ++ |
| Organic residues, ng/ml | 795 | 551 | 260 | 221 | 200 | 175 | 243 | 1013 |

The results of the comparative investigation conducted to study the influence of the prototype composition and the composition as described in the Example 5 on the condition of the face skin.

TABLE 7

The mean percentage of the face skin surface (in the Group), which needs the cosmetic correction

| | Group 1 | Group 2 |
|---|---|---|
| Before the water use | 17.4 | 17.9 |
| In two weeks of the water use | 12.5 | 25.1 |

The results of the blind comparative investigation conducted to study the influence of tap water, of the prototype composition and the composition as described in Example 5 on the condition of skin after 4 weeks of using them in daily hygienic procedures of washing the face skin

TABLE 8

| | Group 1 | Group 2 | Group 3 |
|---|---|---|---|
| pH | 6.2 ± 0.3/ 6.3 ± 0.5 | 6.2 ± 0.3/ 6.1 ± 0.2 | 6.2 ± 0.3/ 5.7 ± 0.3 |
| Elastometry, % | 14.3 ± 0.8/ 13.9 ± 0.6 | 14.3 ± 0.8/ 14.5 ± 0.5 | 14.3 ± 0.8/ 16.3 ± 0.9 |
| Moisture content, % | 33.5 ± 2.4/ 32.5 ± 1.2 | 33.5 ± 2.4/ 37.5 ± 2.0 | 33.5 ± 2.4/ 42.5 ± 2.5 |

Each first figure (before slash)—an indice measured at the beginning of the investigation, the second figure (after slash)—an indice measured at the end of the investigation.

The results of the investigation conducted to compare the effect of using the composition as described in Example 6 with the effects of using the prototype composition, tap water, cleansing tonic and cleansing lotion.

TABLE 9

| Parameter | Cleansing tonic + tap water | Proto-type | Composition as described in Example 6 | Composition as described in Example 6 + cleansing lotion |
|---|---|---|---|---|
| S. Aures | +10% | +25% | −30% | −25% |
| E. Coli | +25% | +15% | −10% | −20% |
| C. Albicans | +10% | +15% | −10% | 0% |
| S. Coagulase (−) | −10% | −20% | +5% | 0% |
| Propionbacter. | −5% | −20% | +5% | +10% |
| Corynebacter. spp | −25% | −30% | +10% | +5% |
| Veilonella spp | −15% | −20% | 0% | 0% |
| pH* | 0% | 0% | −10% | −10% |
| Elastometry, % | 0% | −10% | +15% | +10% |
| Moisture content, % | −5% | 0% | +10% | +5% |

*The mean indice of the face skin acidity before conduction of the investigation comprised 6.2.

The invention claimed is:

1. A composition for washing the face skin, which comprises water, mineral salts and oxygen dissolved in said water, characterized in that it additionally comprises one or several types of essential proteinogenic amino acids with isoelectric point ranging from 3.0 to 6.0 pH, with the following ratio of the ingredients, % of weight:

mineral salts—from 0.01 to 0.1% by weight;
essential proteinogenic amino acids—from 0.01 to 1% by weight;
oxygen dissolved in the water—over 0.001% by weight at a temperature of 22° C.;
a mixture of bacteria representing the normal microflora of human skin, including S.coagulase (−), Aerococcus viridans, Bacillus spp, Burkholderia cepacia, Corynebacterium spp, Acinrtobacter spp, Peptostreptococcus spp, Propionbacterium spp, Veillonella spp in various combinations thereof and in the amounts ranging from $5\text{-}10^{-1}$ to $10\times10^{10}$ CFU in 1 ml; and
water the remainder, wherein the composition has the pH level ranging from 3.0 to 6.0 and its hardness is equal to or less than 0.5 mg-equivalent unit/dm$^3$.

2. Composition as claimed in claim 1, characterized in that it additionally comprises ascorbic acid in the amount from 0.0001 to 10 (% of weight).

3. Composition as claimed in claim 1, characterized in that it additionally comprises provitamin B5 in the amount from 0.0001 to 10 (% of weight).

* * * * *